United States Patent
Carbone, II et al.

(10) Patent No.: US 7,162,749 B2
(45) Date of Patent: Jan. 16, 2007

(54) MECHANICAL FASTENING SYSTEM FOR AN ARTICLE

(75) Inventors: Henry L. Carbone, II, St. Paul, MN (US); Robert L. Popp, Hortonville, WI (US); Debra H. Durrance, Appleton, WI (US); Matthew Lee Koele, Chilton, WI (US); Marcille F. Ruman, Oshkosh, WI (US); Kathleen I. Ratliff, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 600 days.

(21) Appl. No.: 10/319,099

(22) Filed: Dec. 13, 2002

(65) Prior Publication Data

US 2004/0116889 A1    Jun. 17, 2004

(51) Int. Cl.
*A41B 9/14* (2006.01)
*A61B 19/12* (2006.01)
*A41B 9/02* (2006.01)
*A61B 19/08* (2006.01)

(52) U.S. Cl. ............... 2/400; 604/391; 24/442; 24/452; 24/444

(58) Field of Classification Search ........... 604/391, 604/386, 389, 390, 392, 385.24; 24/442, 24/452, 444; 2/96, 236, 400–406; 428/85, 428/90, 91, 96–104

See application file for complete search history.

(56) References Cited

U.S. PATENT DOCUMENTS 4,663,220 A    5/1987   Wisneski et al.
4,704,116 A   11/1987   Enloe
4,940,464 A    7/1990   Van Gompel et al.
5,046,272 A    9/1991   Vogt et al.
5,096,532 A    3/1992   Neuwirth et al.
5,104,116 A    4/1992   Pohjola (Continued)

FOREIGN PATENT DOCUMENTS

EP    0217032 A2    4/1987
EP    0217032 A3    4/1987
EP    0 536 458 A1  4/1993

(Continued)

OTHER PUBLICATIONS

International Search Report for PCT US 03/22201, dated Dec. 9, 2003, 3 pages.

*Primary Examiner*—Gloria M. Hale
(74) *Attorney, Agent, or Firm*—Senniger Powers

(57) ABSTRACT

A mechanical fastening system for an article wherein a first fastening component is secured to the article within an attachment region. A portion of the first fastening component within the attachment region is mechanically bonded to the article, with a ratio of an area of the bonded portion to an area of the attachment region defining a percent bonded area of the first fastening component. A second fastening component is secured to the article within an attachment region thereof. A portion of the second fastening component within the attachment region is mechanically bonded to the article, with a ratio of an area of the bonded portion to an area of the attachment region thereof defining a percent bonded area of the second fastening component. The percent bonded area of the first fastening component is substantially less than the percent bonded area of the second fastening component.

23 Claims, 8 Drawing Sheets

U.S. PATENT DOCUMENTS

| | | |
|---|---|---|
| 5,110,403 A | 5/1992 | Ehlert et al. |
| 5,224,405 A | 7/1993 | Pohjola |
| 5,226,992 A | 7/1993 | Morman |
| 5,660,666 A | 8/1997 | Dilnik et al. |
| 5,766,389 A | 6/1998 | Brandon et al. |
| 5,858,515 A * | 1/1999 | Stokes et al. ............ 428/195.1 |
| 5,897,545 A * | 4/1999 | Kline et al. ................ 604/386 |

FOREIGN PATENT DOCUMENTS

| | | |
|---|---|---|
| EP | 0 658 336 A1 | 6/1995 |
| WO | WO 00/37009 A2 | 6/2000 |
| WO | WO 00/37009 A3 | 6/2000 |
| WO | WO 01/87211 A2 | 11/2001 |
| WO | WO 01/88245 A2 | 11/2001 |

* cited by examiner

MECHANICAL FASTENING SYSTEM FOR AN ARTICLE

BACKGROUND OF THE INVENTION

This invention relates generally to articles such as training pants, diapers, incontinence garments and the like, and more particularly to a mechanical fastening system for such articles and to apparatus and methods for securing the mechanical fastening system to such articles.

Articles such as absorbent articles find widespread use as personal care products including, without limitation, diapers, children's toilet training pants, adult incontinence garments, sanitary napkins and the like, as well as surgical bandages and sponges. These articles absorb and contain body waste and are usually intended to be discarded after a limited period of use; i.e., the articles are not intended to be laundered or otherwise restored for reuse. Conventional absorbent articles comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

Conventional absorbent articles also typically include some type of fastening system for securing the absorbent article in an assembled configuration and/or for fitting the article on the wearer, such on the wearer's waist in the case of diapers and training pants. In many such applications, the fastening system is releasable and refastenable so that the article can be temporarily removed and then refastened to the wearer.

One common form of fastening system is the so-called hook-and-loop fastening system, which comes in various forms and has both advantages and disadvantages in its application to such absorbent articles. For example, particularly when used for training pants, engageable hook and loop fasteners are secured respectively to the front and back waist regions of the article generally at overlapping side panels of the article so that the fasteners releasably engage each other to form the three dimensional shape of the article. In typical such articles, the loop fastener is relatively unstretchable and either forms a portion of the article itself or is attached to the side panel or other component of the article. The hook fastener is generally attached to an extensible substrate (e.g., the side panel) so that it can be suitably positioned in engagement with the loop fastener material while allowing for various shapes and sizes of the intended wearers of the article.

While such hook-and-loop fastener systems have proven effective, some hook fasteners may have a tendency to disengage or separate from the loop fasteners when the wearer is active, such as when stooping or bending as is common with a child in training pants or diapers. This separation can result in the article coming loose from the wearer (with possible leakage resulting), thus requiring the article to be refitted and refastened, if possible, or simply replaced.

SUMMARY OF THE INVENTION

In general, one embodiment of a mechanical fastening system for an article comprises a first fastening component secured to the article within an attachment region of the first fastening component, the attachment region having an area. A bonded portion of the first fastening component within the attachment region is mechanically bonded to the article and the remaining portion of the first fastening component within the attachment region is substantially mechanically unbonded to the article. The bonded portion has an area within the attachment region, with a ratio of the area of the bonded portion to the area of the attachment region defining a percent bonded area of the first fastening component within the attachment region. A second fastening component is secured to the article and is adapted for releasable engagement with the first fastening component to assemble the article. The second fastening component is secured to the article within an attachment region of the second fastening component, with the attachment region having an area. A bonded portion of the second fastening component within the attachment region is mechanically bonded to the article and the remaining portion of the second fastening component within the attachment region is substantially mechanically unbonded to the article. The bonded portion has an area within the attachment region, wherein a ratio of the area of the bonded portion of the second fastening component to the area of the attachment region thereof defines a percent bonded area of the second fastening component within the attachment region. The percent bonded area of the first fastening component is substantially less than the percent bonded area of the second fastening component.

In another embodiment, a mechanical fastening system for an article generally comprises a first fastening component secured to the article along an attachment region of the first fastening component, with the attachment region having an area. A bonded portion of the first fastening component within the attachment region is mechanically bonded to the article and the remaining portion of the first fastening component within the attachment region is substantially mechanically unbonded to the article. The bonded portion of the first fastening component within the attachment region thereof comprises a plurality of discrete bond points at which the first fastening component is mechanically bonded to the article. A ratio of the number of bond points within the attachment region to the area of the attachment region defines an average bond point density of the first fastening component within the attachment region thereof. A second fastening component is secured to the article and is adapted for releasable engagement with the first fastening component to assemble the article. The second fastening component is secured to the article within an attachment region of the second fastening component, with the attachment region having an area. A bonded portion of the second fastening component within the attachment region is mechanically bonded to the article and the remaining portion of the second fastening component within the attachment region is substantially mechanically unbonded to the article. The bonded portion of the second fastening component within the attachment region thereof comprises a plurality of discrete bond points at which the second fastening component is mechanically bonded to the article. A ratio of the number of bond points within the attachment region to the area of the attachment region defines an average bond point density of the second fastening component within the attachment region thereof. The average bond point density of the first fastening component is less than the average bond point density of the second fastening component.

One embodiment of a method of making articles generally comprises transporting at least one article in a machine direction during assembly of the article. At least one first fastening component is positioned on the article and at least one second fastening component is also positioned on the article. The at least one second fastening component is positioned in spaced relationship with the at least one first fastening component in the machine direction, and is releasably engageable with the at least one first fastening component. The at least one first fastening component is secured to the article within an attachment region of the first fastening component, the securing step comprising mechanically bonding a portion of the first fastening component within the attachment region thereof to the article. The bonded portion comprises less than the entire attachment region, and a ratio of an area of the bonded portion to an area of the attachment region defines a percent bonded area of the first fastening component within the attachment region thereof. The at least one second fastening component is secured to the article within an attachment region of the second fastening component, the securing step comprising mechanically bonding a portion of the second fastening component within the attachment region thereof to the article. The bonded portion comprises less than the entire attachment region, and a ratio of an area of the bonded portion to an area of the attachment region defines a percent bonded area of the second fastening component within the attachment region thereof. The percent bonded area of the second fastening component is greater than the percent bonded area of the first fastening component.

An article of one embodiment of the present invention generally comprises a first waist region, a second waist region and a crotch region disposed between and interconnecting the first and second waist regions. At least one first fastening component is secured to the article generally at the first waist region within an attachment region of the first fastening component, the attachment region having an area. The bonded portion of the first fastening component within the attachment region is mechanically bonded to the article and the remaining portion of the first fastening component within the attachment region is substantially mechanically unbonded to the article. The bonded portion has an area within the attachment region, and a ratio of the area of the bonded portion to the area of the attachment region defines a percent bonded area of the first fastening component within the attachment region. At least one second fastening component is secured to the article and is adapted for releasable engagement with the first fastening component to assemble the article. The second fastening component is secured to the article generally at the second waist region within an attachment region of the second fastening component, the attachment region having an area. A bonded portion of the second fastening component within the attachment region is mechanically bonded to the article and the remaining portion of said second fastening component within the attachment region is substantially mechanically unbonded to the article. A ratio of an area of the bonded portion to an area of the attachment region defines a percent bonded area of the second fastening component within the attachment region. The percent bonded area of the first fastening component is less than the percent bonded area of the second fastening component.

In general, apparatus for mechanically bonding first and second fastening components to an article generally comprises a first bonding segment adapted to mechanically bond a portion of the first fastening component to the article within an attachment region of the first fastening component whereby the remaining portion of the first fastening component within the attachment region thereof is free of mechanical bonding to the article. A ratio of an area of the bonded portion of the first fastening component to an area of the attachment region thereof defines a percent bonded area of the first fastening component. A second bonding segment is adapted to mechanically bond a portion of the second fastening component to the article within an attachment region of the second fastening component whereby the remaining portion of the second fastening component within the attachment region thereof is free of mechanical bonding to the article. A ratio of an area of the bonded portion of the second fastening component to an area of the attachment region thereof defines a percent bonded area of the second fastening component. The percent bonded area of the first fastening component is less than the percent bonded area of the second fastening component.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Inward" and "outward" refer to positions relative to the center of an article, and particularly transversely and/or longitudinally closer to or away from the longitudinal and transverse center of the article.

"Layer" when used in the singular can have the dual meaning of a single element or a plurality of elements.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Permanently bonded" refers to the joining, adhering, connecting, attaching, or the like, of two elements of an article such that the elements tend to be and remain bonded during normal use conditions of the article.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portions of the specification.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
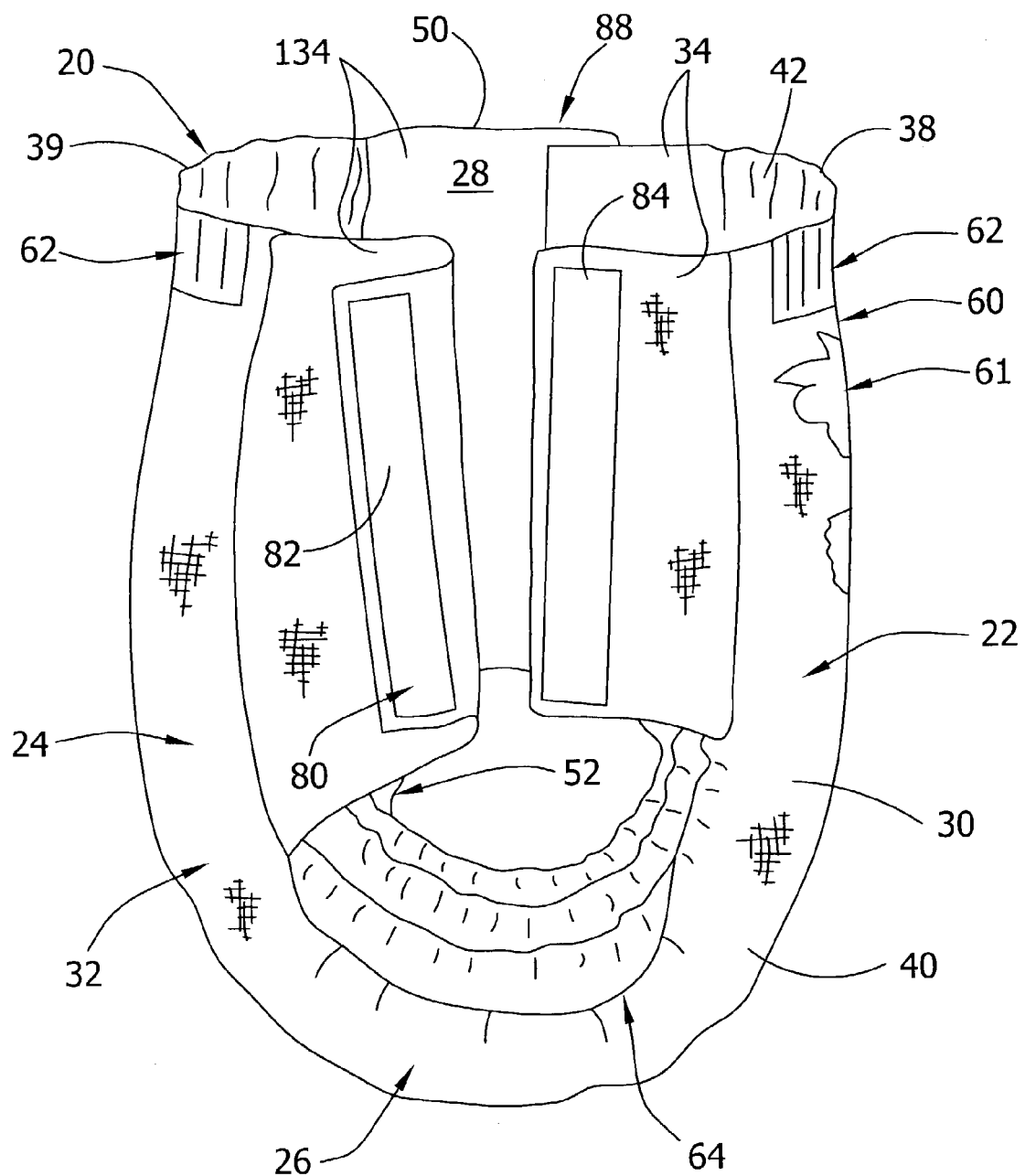
FIG. 1 is a side view of a pair of training pants having a mechanical fastening system of the present invention shown fastened on one side of the training pants and unfastened on the other side of the training pants.

Referring now to the drawings and in particular to FIG. 1, an article in the form of children's toilet training pants is indicated in its entirety by the reference numeral 20 and incorporates a mechanical fastening system, generally indicated at 80, of the present invention for securing the pants in an assembled, three dimensional form. The article may or may not be absorbent and may or may not be disposable, which generally refers to absorbent articles that may be placed against or in proximity to the body of the wearer to absorb and/or retain various liquid waste discharged from the body. Such articles are intended to be discarded after a limited period of use instead of being laundered or otherwise restored for reuse. While the fastening system 80 of the present invention is shown and described herein in connection with children's toilet training pants, it is understood that the fastening system may be incorporated into various other articles such as diapers, training pants, feminine hygiene products, incontinence products, medical articles, other personal care or health care garments, swim pants, athletic clothing, pants and shorts, and the like without departing from the scope of the present invention.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The pair of training pants 20 is illustrated in FIG. 1 in a partially fastened condition and comprises a front waist region 22, a back waist region 24, a crotch region 26 interconnecting the front and back waist regions, an inner surface 28 configured for contiguous relationship with the wearer, and an outer surface 30 opposite the inner surface. With additional reference to FIGS. 2 and 3, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
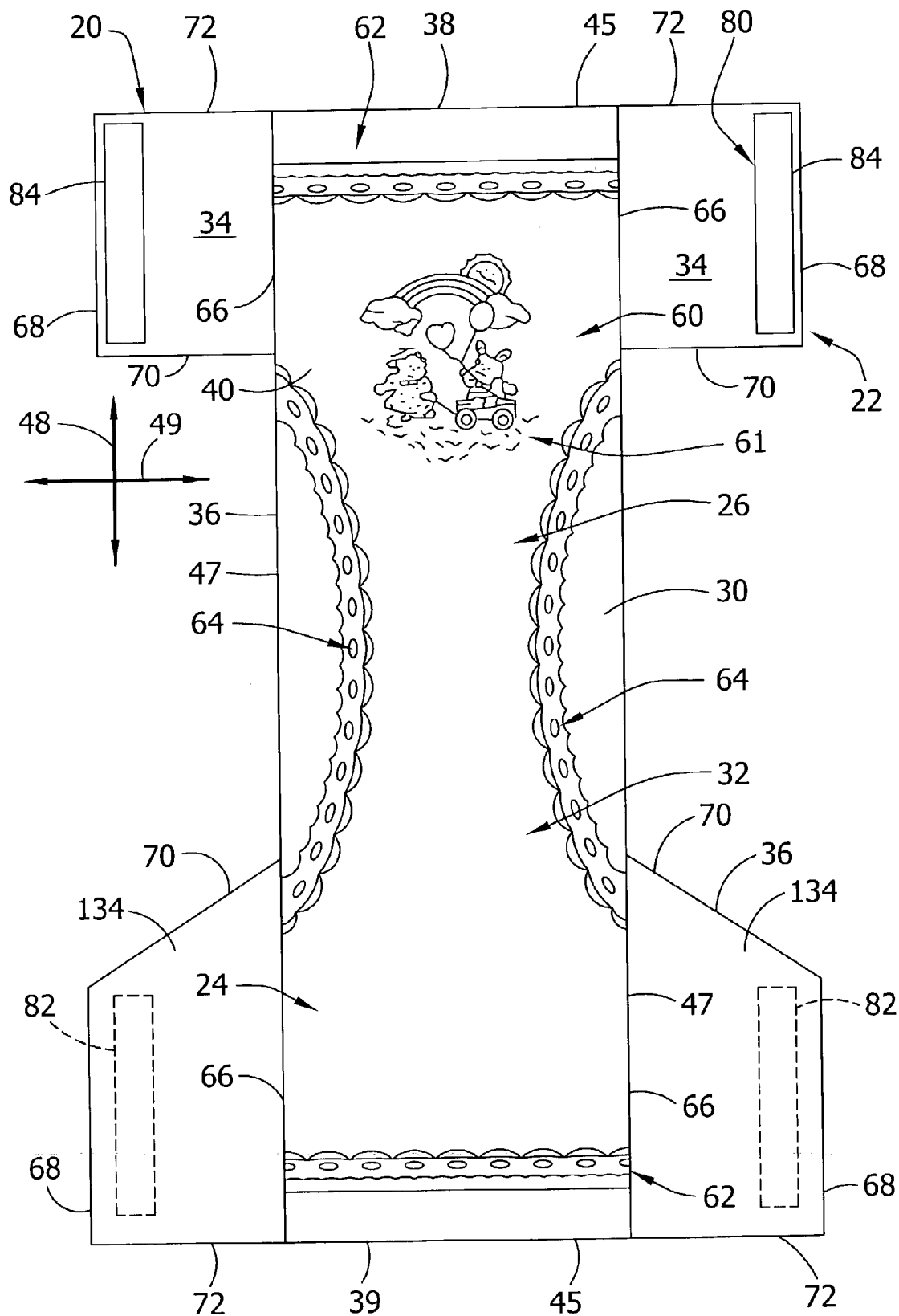
FIG. 2 is a plan view of the training pants shown in FIG. 1 in an unfastened, stretched and laid flat condition, and showing the surface of the training pants that faces away from the wearer.
Figure 3:
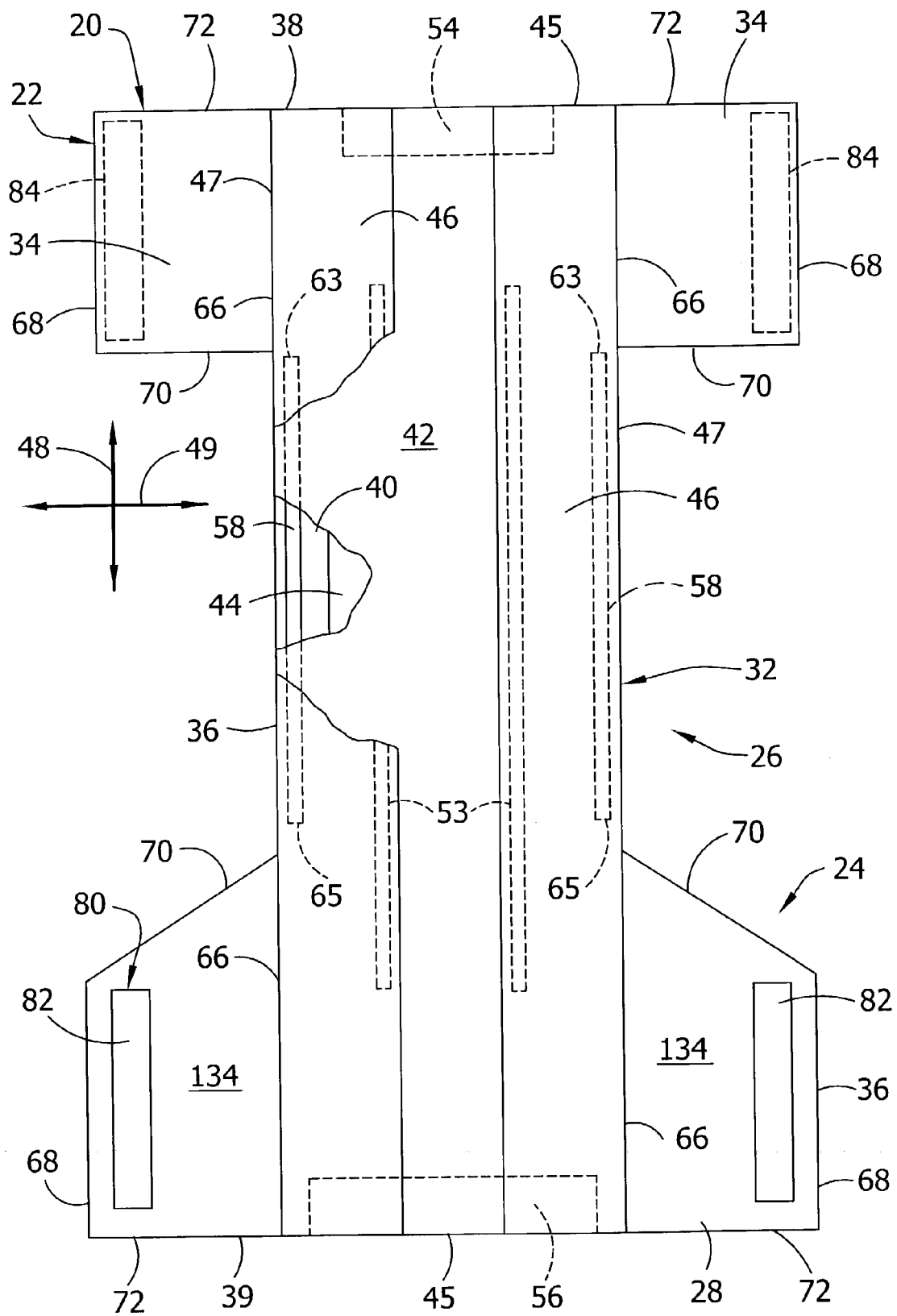
FIG. 3 is a plan view similar to FIG. 3, but showing the surface of the training pants that faces the wearer when worn, and with portions cut away to show underlying features.

The illustrated pants 20 comprises a central absorbent assembly 32, which when laid flat can be rectangular or any other desired shape, a pair of laterally opposite front side panels 34 extending outward therefrom at the front waist region and a pair of laterally opposite back side panels 134 extending outward therefrom at the back waist region. The absorbent assembly 32 and side panels 34, 134 may comprise two or more separate elements, as shown in FIG. 1, or be integrally formed. The central absorbent assembly 32 of the illustrated embodiment comprises an outer cover 40, a bodyside liner 42 (FIGS. 1 and 3) connected to the outer cover in a superposed relation, an absorbent body 44 (FIG. 3) disposed between the outer cover and the bodyside liner, and a pair of containment flaps 46 (FIG. 3). The central absorbent assembly also has opposite ends 45 which form portions of the front and back waist edges 38 and 39, and opposite side edges 47 which form portions of the side edges 36 of the training pants 20 (FIGS. 2 and 3). Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pants. For further reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by the fastening system 80 to define a three-dimensional pants configuration having a waist opening 50 and a pair of leg openings 52. The front waist region 22 comprises the portion of the training pants 20 which, when worn, is positioned on the front of the wearer while the back waist region 24 comprises the portion of the training pants which is positioned on the back of the wearer. The crotch region 26 of the training pants 20 comprises the portion of the training pants 20 which is positioned between the legs of the wearer and covers the lower torso of the wearer. The front and back side panels 34 and 134 comprise the portions of the training pants 20 which, when worn, are positioned on the hips of the wearer. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb any exudates discharged from the wearer. For example, the absorbent assembly 32 desirably although not necessarily further comprises the containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily includes a front waist elastic member 54 (FIG. 3), a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumberg, Ill., U.S.A.

If the outer cover 40 is a single layer of material, it can be embossed and/or matte finished to provide a more cloth-like appearance. As earlier mentioned, the liquid impermeable material can permit vapors to escape from the interior space 51 of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 desirably comprises one or more appearance-related components. Examples of appearance-related components include, but are not limited to, graphics; highlighting or emphasizing leg and waist openings 52, 50 in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of training pants 20 is designed for use by young girls and includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent body 44, and may but need not have the same dimensions as the outer cover 40. The bodyside liner 42 is desirably compliant, soft feeling, and non-irritating to the child's skin. Further, the bodyside liner 42 can be less hydrophilic than the absorbent body 44, to present a relatively dry surface to the wearer and permit liquid to readily penetrate through its thickness. Alternatively, the bodyside liner 42 can be more hydrophilic or can have essentially the same affinity for moisture as the absorbent body 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent body 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants 20 can comprise elastomeric or nonelastomeric materials.

The absorbent body 44 (FIG. 3) is positioned between the outer cover 40 and the bodyside liner 42, which can be joined together by any suitable means such as adhesives, ultrasonic bonds, thermal bonds, or the like. The absorbent body 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 44 can suitably comprise a matrix of hydrophilic fibers, such as a web of cellulosic fluff, mixed with particles of a high-absorbency material commonly known as superabsorbent material. In a particular embodiment, the absorbent body 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be non-uniformly mixed. The fluff and superabsorbent particles can also be selectively placed into desired zones of the absorbent body 44 to better contain and absorb body exudates. The concentration of the superabsorbent particles can also vary through the thickness of the absorbent body 44. Alternatively, the absorbent body 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent body 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent body 44 in an amount of from 0 to about 90 weight percent based on total weight of the absorbent assembly. The absorbent body 44 suitably has a density within the range of about 0.10 to about 0.35 grams per cubic centimeter. The absorbent body 44 may or may not be wrapped or encompassed by a suitable tissue wrap that may help maintain the integrity and/or shape of the absorbent assembly.

The central absorbent assembly 32 can also incorporate other materials designed primarily to receive, temporarily store, and/or transport liquid along the mutually facing surface with the absorbent body 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent assembly 32. The side panels 34, 134 can be permanently bonded along seams 66 to the central absorbent assembly 32 in the respective front and back waist regions 22 and 24. More particularly, as seen best in FIGS. 2 and 3, the front side panels 34 can be permanently bonded to and extend transversely outward beyond the side edges 47 of the absorbent assembly 32 in the front waist region 22, and the back side panels 134 can be permanently bonded to and extend transversely outward beyond the side edges of the absorbent assembly in the back waist region 24. The side panels 34 and 134 may be bonded to the absorbent assembly 32 using attachment means known to those skilled in the art such as adhesive, thermal or ultrasonic bonding. Alternatively, the side panels 34 and 134 can be formed as an integral portion of a component of the absorbent assembly 32. For example, the side panels can comprise a generally wider portion of the outer cover 40, the bodyside liner 42, and/or another component of the absorbent assembly 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the training pants 20, and the waist end edges 72 of the back side panels 134 form part of the back waist edge 39 of the pants.

In particular embodiments for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in training pants 20 having an overall length of about 54 centimeters, the side panels 34, 134 desirably have a length in the range of about 6 centimeters to about 20 centimeters. While each of the side panels 34, 134 extends from the waist opening 50 to one of the leg openings 52, the illustrated back side panels 134 have a continually decreasing length dimension moving from the attachment line 66 to the outer edge 68, as is best shown in FIGS. 2 and 3.

Each of the side panels 34, 134 can include one or more individual, distinct pieces of material. In particular embodiments, for example, each side panel 34, 134 can include first and second side panel portions that are joined at a seam, or can include a single piece of material which is folded over upon itself (not shown).

The side panels 34, 134 desirably although not necessarily comprise an elastic material capable of stretching in a direction generally parallel to the transverse axis 49 of the training pants 20. Suitable elastic materials, as well as one process of incorporating elastic side panels into training pants, are described in the following U.S. Pat. No.: 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Pat. No. Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks.

Loop fasteners typically comprise a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes et al. incorporated herein by reference. The loop material may be secured to a base, or backing structure and the composite then secured to the pants 20, or the loop material may be secured directly to the pants so that pants serves as a backing for the loop material, or the loop material may be formed integrally with the pants, such as by constructing one or more layers or surfaces of the back side panels 134 from a loop material.

Hook fasteners typically comprise a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructively releasable engagement. In contrast to the loop fasteners which desirably comprise a flexible fabric, the hook material may advantageously comprise a resilient material to minimize unintentional disengagement of the fastening components 82, 84 as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may formed integrally with the pants 20, and more particularly with the side panels 34, without departing from the scope of this invention.

With particular reference to FIG. 3, the first fastening components 82 (e.g., the loop fasteners) are disposed on the inner surface 28 of the back side panels 134, and are desirably positioned along the outer edges 68 of the back side panels 134 in generally abutting or adjacent relationship with the waist end edge 72. In certain embodiments, for example, the fastening components 84 can be spaced inward from the outer edges 68 of the back side panels 134 in the range of about 0 to 25 mm. With particular reference to FIG. 2, the second fastening components 84 (e.g., the hook fasteners) are disposed on the outer surface 30 of the front side panels 34, and are desirably sized to receive the first fastening components 82. The fastening components 84 are also desirably positioned along the outer edges 68 of the front side panels 34 in abutting or adjacent relationship with the waist end edge 72. As an example, the second fastening components 84 can be spaced inward from the outer edges 68 of the front side panels 34 in the range of about 0 to 25 mm. It is understood that the fastening components 82, 84 may also extend laterally out beyond the outer edges 68 of the side panels 134, 34. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 82, 84 of the illustrated embodiments are rectangular, although they may alternatively be square, round, oval, curved or otherwise non-rectangularly shaped. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 50 to about 130 mm, such as about 100 mm, and the width is desirably from about 5 to about 30 mm, such as about 10 mm. In particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

The fastening components 84, 82 are desirably secured to the respective side panels 34, 134 by mechanical bonding. As used herein, mechanical bonding refers to non-adhesive bonding, such as by the application of pressure, ultrasonic energy, heat, laser energy or any other suitable form of energy which joins the fastening components to the side panels. It is understood that the fastening components 84, 82 may be adhered, such as by adhesive or cohesive means, to the respective side panels 34, 134 in addition to being mechanically bonded thereto, or the fastening components may only be mechanically bonded to the side panels, without departing from the scope of this invention. Where a fastening component 82, 84 is formed integrally with the respective side panel 134, 34, the mechanical bonding comprises mechanically bonding the fastener material layer of the side panel to one more other layers or surfaces of the side panel.

More particularly, the mechanical bonding is applied over an "attachment region" 85 (FIGS. 9 and 10) of each fastening component 82, 84. The attachment region 85 is defined herein as being that region of the fastening component 82, 84 in which mechanical bonding is present. It is understood, and even desired as will be discussed, that the entire fastening component 82, 84 within the attachment region 85 need not actually be mechanically bonded to the respective side panel 134, 34.

Figure 9:
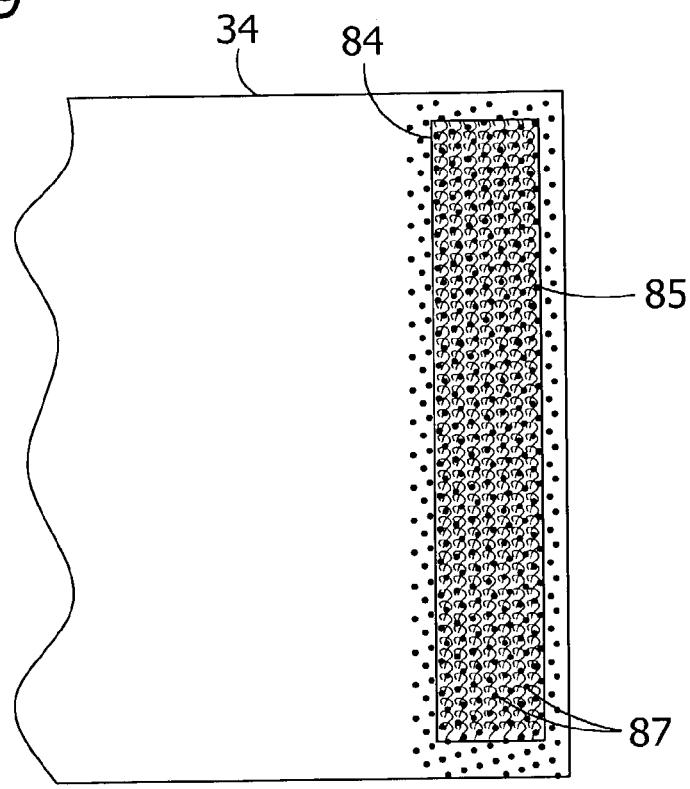
FIG. 9 is a plan view of a portion of the training pants of FIG. 2 showing a fastening component bonded to a side panel of the pants in accordance with one embodiment of the invention.
Figure 10:
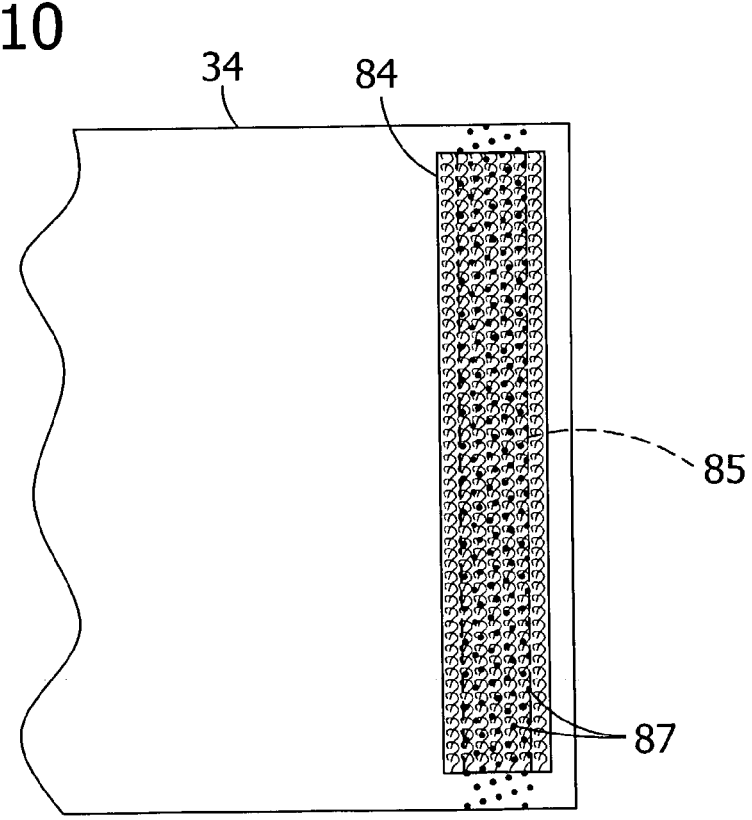
FIG. 10 is a plan view of a portion of the training pants of FIG. 2 showing a fastening component bonded to a side panel of the pants in accordance with another embodiment of the present invention.

As an example, with reference to FIG. 9, where the mechanical bonding of the fastening component 84 to the side panel 34 is present up to or even beyond the side edges and ends of the fastening component, the attachment region 85 is defined by the dimensions of the fastening component itself. Where less than the entire fastening component 84 is subjected to mechanical bonding, such as illustrated in FIG. 10, the attachment region 85 is bounded by the outermost (e.g., the laterally inner and outermost in FIG. 10) mechanical bonds on the fastening component. The attachment region 85 therefore has an area defined by the dimensions (e.g., length and width in the illustrated embodiments of FIGS. 9 and 10) of the attachment region. Where the fastening component 82, 84 is formed integrally with the side panel 134, 34, this would comprise bonding the layers of the fastening component to the remaining side panel layers or surfaces.

As stated previously, it is desirable that only a portion of the fastening component 82, 84 within the attachment region 85 is actually mechanically bonded to the respective side panel 134, 34, with the rest of the fastening component within the attachment region remaining substantially mechanically unbonded to the side panel. It is understood from the definition of mechanically bonded provided above that the term mechanically unbonded as used herein is intended to mean that the fastening component 82, 84 is free of any mechanical bonding to the respective side panel 134, 34, though the fastening component may still be adhesively secured to the respective side panel.

Mechanical bonding techniques, such as ultrasonic bonding, typically damage a certain portion of the hook and loop elements of the respective fastening components 82, 84, thereby causing some reduced engagement strength therebetween. Thus, it is desired that the bonded portion within the attachment region 85 be sufficient to secure the fastening components to the respective side panels 34, 134 but without damaging an excessive portion of the associated hook and loop elements. More particularly, it is desirable to control the amount of hook and loop elements damaged by the mechanical bonds such that shear and peel forces caused by the movements of the wearer do not disengage the fastening components 82, 84 from each other, while maintaining a sufficient bonded portion of each fastening component to inhibit separation of the fastening components from the side panels 34, 134.

In the illustrated embodiments of FIGS. 9 and 10, the mechanically bonded portion of each fastening component 82, 84 is defined by a plurality of discrete bond points 87 (FIGS. 9 and 10) whereby the mechanically unbonded portion of the fastening component within the attachment region 85 thereof is generally continuous around the discrete bond points 87. Each of the discrete bond points 87 has a cross-sectional area, e.g., measured in the plane of the fastening component. The sum of the areas of all of the bond points 87 within the attachment region 85 defines a bonded area of the bonded portion of the fastening component which is less than the area of the overall attachment region of the fastening component. The ratio of the bonded area to the area of the attachment region defines a "percent bonded area" of the fastening component which may be determined as follows:

$$\text{Percent Bonded Area} = \frac{(\text{Area of Bonded Portion within Attachment Region})}{(\text{Area of Attachment Region})} \times 100$$

Even more desirably, the percent bonded area of each of the first fastening components 82 is less than the percent bonded area of each of the second fastening components 84. For example, in the illustrated embodiment where the first fastening component 82 is a loop fastener and the second fastening component is a hook fastener, the percent bonded area of the loop fastener is desirably less than or equal to about twenty percent, more desirably less than about six percent, still more desirably in the range of about 3.4 to about 4.5 percent, and even more desirably about 3.9 percent. The percent bonded area of the hook fastener is desirably greater than the percent bonded area of the loop fastener and is in the range of about one to about thirty percent, more desirably in the range of about three to about ten percent, still more desirably in the range of about 3.6 to about 5.4 percent, and even more desirably about 4.5 percent.

The discrete bond points 87 of the fastening components 82, 84 also define respective bond densities of the fastening components, with the "bond density" of each fastening component being defined as the total number of bond points within the attachment region 85 of the fastening component divided by the area of the attachment region of the fastening component. Desirably, the bond density of each of the first fastening components 82 is less than the bond density of each of the second fastening components 84. For example, in the illustrated embodiment where the first fastening components are loop fasteners and the second fastening components are hook fasteners, the bond density of each loop fastener is desirably in the range of about 1 bond/cm$^2$ to about 50 bonds/cm$^2$, and more desirably about 5 bonds/cm$^2$. The bond density of each hook fastener is desirably in the range of about 1 bond/cm$^2$ to about 50 bonds/cm$^2$, and more desirably about 6 bonds/cm$^2$.

In the illustrated embodiments of FIGS. 9 and 10, the discrete bond points 87 of the fastening components 82, 84 define generally uniform bond point patterns. However, it is understood that the bond points 87 may define a generally irregular or otherwise non-uniform pattern without departing from the scope of this invention. For example, it is contemplated that the bond point 87 pattern may be such that the bond density is substantially non-uniform across the width and/or along the length of the respective fastening component 82, 84, as long as the first fastening components each have an overall, or average bond density which is less than the overall, or average bond density of each of the second fastening components.

The bond points 87 may be substantially of any shape, such as circular, square, rectangular, triangular, star-shaped or other suitable shape. It is also contemplated that the size of the bond points 87 that define the bonded portion of the first fastening component 82 may be different, e.g., larger or smaller, than the bond points that define the bonded portion of the second fastening component 84. For example, the cross-sectional area of each bond point 87 may be in the range of about 0.002 cm$^2$ to about 0.051 cm$^2$, and more particularly about 0.013 cm$^2$. It is therefore understood that in one embodiment the bond densities of the first and second fastening components 82, 84 may be the same, but the bond points 87 of the second fastening component may be larger in cross-sectional area than the bond points of the first fastening component so that the percent bonded area of the second fastening component is greater than the percent bonded area of the first fastening component. In another embodiment, the sizes (e.g., cross-sectional areas) of the bond points 87 of the fastening components 82, 84 may be the same, but the bond density of the second fastening component is greater than the bond density of the first fastening component so that the percent bonded area of the second fastening component is greater than that of the first fastening component. It is also understood that the size of the bond points 87 may be non-uniform across the width and/or along the length of each fastening component 82, 84.

While the bonded portion with the attachment region 85 of each fastening component 82, 84 is illustrated and described herein as comprising discrete bond points 87, it is contemplated that the bonded portion of each fastening component may instead be substantially continuous to thereby define a mechanically unbonded portion of the fastening component comprising a plurality of discrete mechanically unbonded points within the attachment region. In such an embodiment, the bonded area of the fastening component 82, 84 is defined as the total area of the continuous bonded portion within the attachment region 85 of the fastening component. One way to determine the bonded area would be to sum the cross-sectional areas of the unbonded points within the attachment region 85 and subtract this sum from the area of the attachment region.

As shown in FIG. 1, when the fastening components 82, 84 are releasably engaged, the side edges 36 of the training pants 20 in the crotch region 26 define the leg openings 52, and the waist edges 38 and 39 including the waist end edges 72 of the side panels 34, 134 define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When engaged, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 70 to 100 percent, and particularly about 85 to about 95 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 70 to 100 percent, and more particularly about 85 to about 95 percent, of the distance between the waist end edge 70 and the leg end edge 72 of the side panels 34, 134. In other embodiments, the fastening components can comprise a plurality of smaller fastening elements (not shown) covering a smaller portion of the distance between the waist opening 50 and the leg openings 52, for example, about 20 to about 70 percent, but spaced apart to span a larger percentage of the distance between the waist opening and the leg openings.

For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between each respective set of fastening components 82, 84 is measured parallel to the transverse axis 49 between the longitudinal center lines of the respective fastening components, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may be only partially laterally opposite each other, such as by being offset longitudinally, without departing from the scope of this invention.

Figure 4:
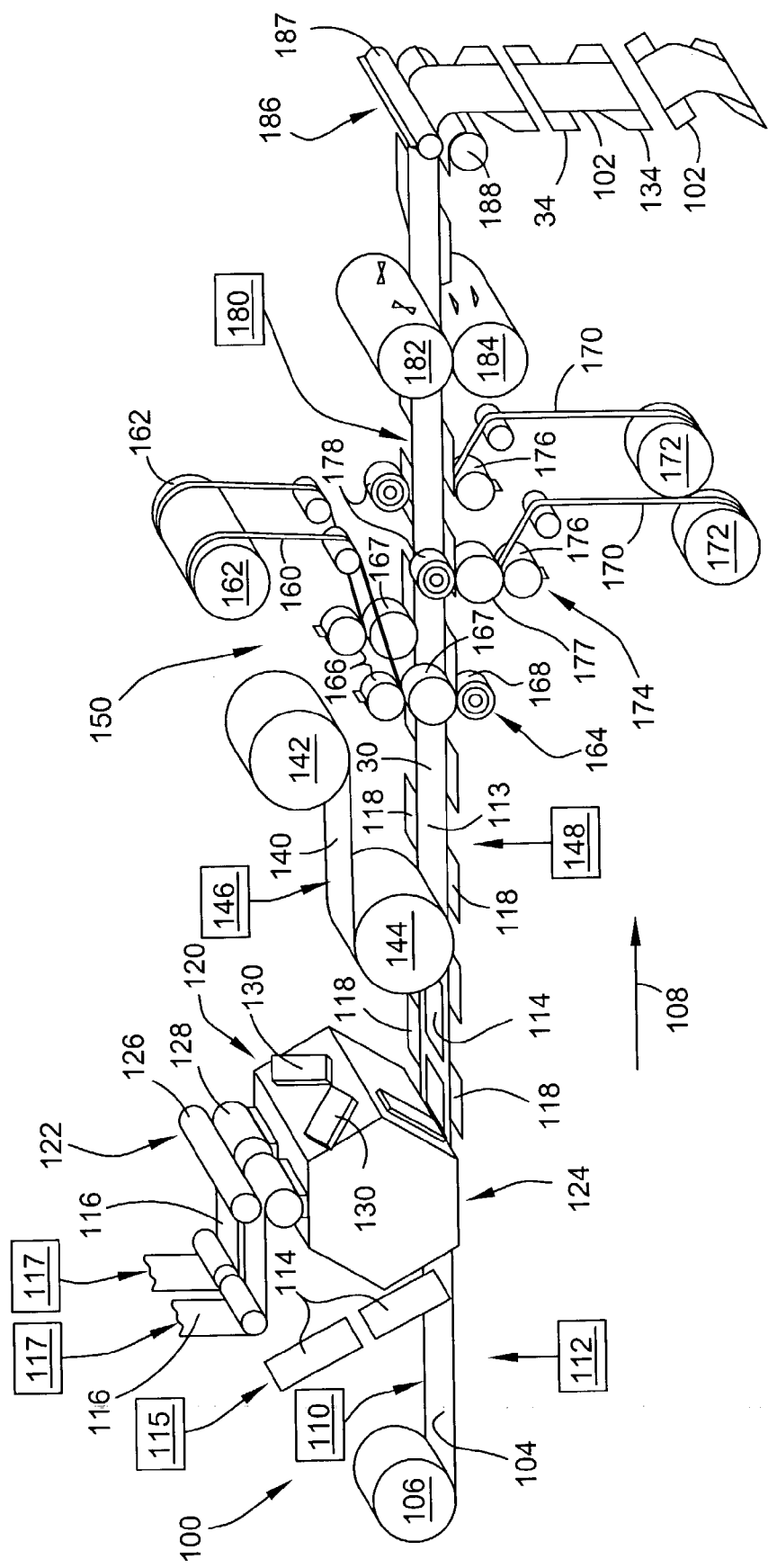
FIG. 4 is a schematic view of one embodiment of apparatus for making training pants according to the present invention.

FIG. 4 is an apparatus 100 for making a continuous stream of partially assembled, discrete training pants 20 with a fastening system 80 of the present invention. The particular method and apparatus described herein in relation to FIG. 4 is particularly suited to manufacture training pants 20 of the type illustrated in FIG. 1. However, the specific components of the apparatus 100 may vary depending on the specific type of absorbent article being manufactured.

The various components of the training pants 20 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain article manufacturing equipment which is readily known and understood in the art, including frames and mounting structures, transport conveyors, transfer rolls, guide rolls, tension rolls, and the like, have not been shown in FIG. 4. Suitable absorbent supply mechanisms, web unwinds, conveyor systems, registration systems, drive systems, control systems, cutting systems and the like, for use with the present process are disclosed in U.S. patent application Ser. No. 09/855,484 entitled "Methods for Making Garments with Fastening Components" and filed May 15, 2001, and U.S. Pat. No. 5,766,389 issued Jun. 16, 1998 to Brandon et al., which are hereby incorporated herein by reference.

In the illustrated embodiment, a continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components of the pants 20 can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The continuously moving product assemblage 113 defines a longitudinal center line 105 (FIG. 5) which can correspond to the machine center line. The product assemblage 113 will be cut downstream to form the partially assembled, discrete training pants 20.

A plurality of absorbent bodies 114 can be provided from a suitable supply source 115. The supply source 115 can be any conventional mechanism for supplying the absorbent bodies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent bodies 114 can be disposed intermittently on the continuously moving bodyside liner material 104, one for each pair of training pants. The position of the absorbent bodies 114 can be registered with the position of the surge layer, if employed. The absorbent bodies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118, also referred to as side panel strips 118, and positioned partially on the bodyside liner material 104 using an applicator device 120. In the cross machine direction, the individual strips 118 desirably extend laterally outward from the bodyside liner material 104 (see FIG. 5) and overlap the bodyside liner material by an amount such as about 2 cm or more to permit bonding of the strips to the bodyside liner and/or the containment flap material. In the machine direction 108, the position of the strips 118 can be registered relative to the absorbent bodies 114 so that the product assemblage 113 can be cut between the absorbent bodies with each strip 118 of side panel material 116 forming both a front side panel 34 and a back side panel 134 of consecutive articles 102.

One suitable applicator device 120 is disclosed in U.S. Pat. Nos. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels 34, 134 can alternatively be provided in continuous form and pressurized fluid-jets or a rotary die cutter can be employed to cut the material to form leg openings 52. Still alternatively, the side panels 34 and 134 of the training pants 20 can be provided by portions of the bodyside liner 42 and/or outer cover 40. By any of the foregoing methods, the resulting product assemblage 113 can have a plurality of pairs of opposed side panel strips 118. Each pair has a side panel strip 118 extending transversely outward from the longitudinal center line 105 on each side of the longitudinal center line. The side panel strips 118 forming each pair are at the same machine direction location, and the plurality of pairs of opposed side panel strips, or at least their widest portions, are spaced from one another in the machine direction 108.

A continuous supply of material 140 used to form the outer cover 40 can be provided from a supply roll 142 or other suitable source. The outer cover material 140 can be transported over a laminator roll 144 and married with the bodyside liner material 104. The absorbent bodies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104, 140. Alternatively, leg elastics or waist elastics can be initially bonded to the bodyside liner material 104 or another material.

Bonding devices 148 such as ultrasonic bonding devices can be employed downstream of the laminator roll 144 to bond the bodyside liner material 104, side panel material 116 and outer cover material 140. For example, these materials can be transported between a conventional rotary ultrasonic horn and anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 cm and a width of from about 2 to about 15 cm. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

Figure 5:
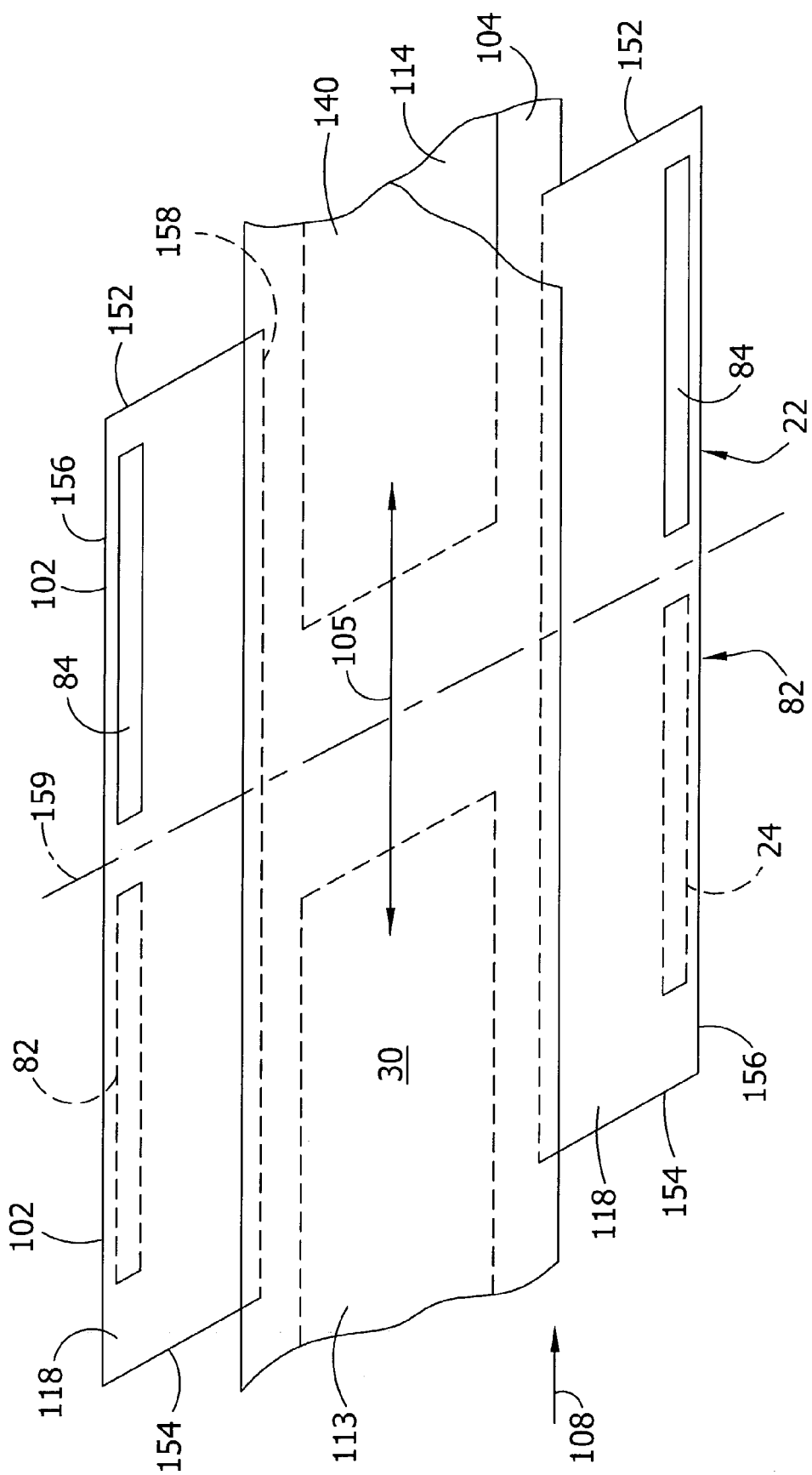
FIG. 5 is a portion of a product assemblage at one point in the process illustrated in FIG. 4.

The continuously moving product assemblage 113 next advances to a fastener application station 150 where fastening components 82, 84 are positioned on and bonded to the strips 118 of side panel material 116. The location of the fastening components on the composite is a function in part of the configuration of the apparatus 100. The illustrated apparatus 100 is configured so that the upwardly facing major surface of the product assemblage 113 will become the outer surface 30 of the training pants 20 and the downwardly facing major surface will become the inner surface 28. Moreover, the illustrated apparatus 100 is configured to produce partially assembled training pants 20 having the front waist region 22 of a leading pair of pants 20 connected to the back waist region 24 of a trailing pair as shown in FIG. 5. The process could alternatively employ any combination of different orientations. For example, the upwardly facing surface of the product assemblage could form the inner surface 28 of finished articles. Additionally or alternatively, the back waist region 24 of a leading pair of pants 20 can be connected to the front waist region 22 of the trailing pair of pants 20, or the pair of pants 20 can be arranged in a front-to-front/back-to-back relationship. Still alternatively, the apparatus 100 could be constructed as a cross-machine direction process wherein the longitudinal axis 48 of each pair of pants 20 could be perpendicular to the machine direction 108 during part or all of the assembly process.

The location of the fastening components 82, 84 in this embodiment is best illustrated in FIG. 5, which shows a portion of the product assemblage 113 moving in the direction of arrow 108 immediately following application of the fastening components 82, 84 to the product assemblage. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 20. Based on the illustrated orientation of the continuously moving product assemblage 113, the first fastening components 82 can be positioned on and bonded to the underside of the strips 118 corresponding to the back side panels 134 and the second fastening components 84 can be positioned on and bonded to the top surface of the strips corresponding to the front side panels 34. The first fastening components 82 are desirably disposed on opposite sides of the longitudinal center line 105 at selected cross machine direction locations, and the second fastening components 84 are desirably disposed on opposite sides of the longitudinal center line 105 at the same selected cross machine direction locations as the first fastening components 82. For purposes of the present invention, the term "cross machine direction location" refers to a location spaced from the machine center line, measured perpendicular thereto. The cross machine direction location of each fastening component 82, 84 encompasses the width dimension of the fastening component, where the width dimension is disposed in the cross machine direction.

With reference again to FIG. 4, continuous webs of second fastener material 160 used to form the second fastening components 84 can be provided from supply rolls 162 or other suitable sources. The second fastener materials 160 can be cut into individual second fastening components by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 can be provided from supply rolls 172 or other suitable sources. The first fastener materials 170 can be cut into individual first fastening components 82 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

After the fastening components are disposed on the strips 118 of side panel material 116, apparatus of the present invention can be employed to mechanically bond the first fastener material 170 and the second fastener material 160 to the strips 118. In the illustrated embodiment, the apparatus comprises a pair of mechanical bonding devices 180, and more particularly a pair of ultrasonic bonding devices as will be described. The fastening components 82, 84 can be maintained on the side panel strips 118 until reaching the bonding devices 180 with suitable vacuum devices (not shown), or can be attached to the side panel strips at the fastener application station 150 with adhesive bonds.

Figure 6:
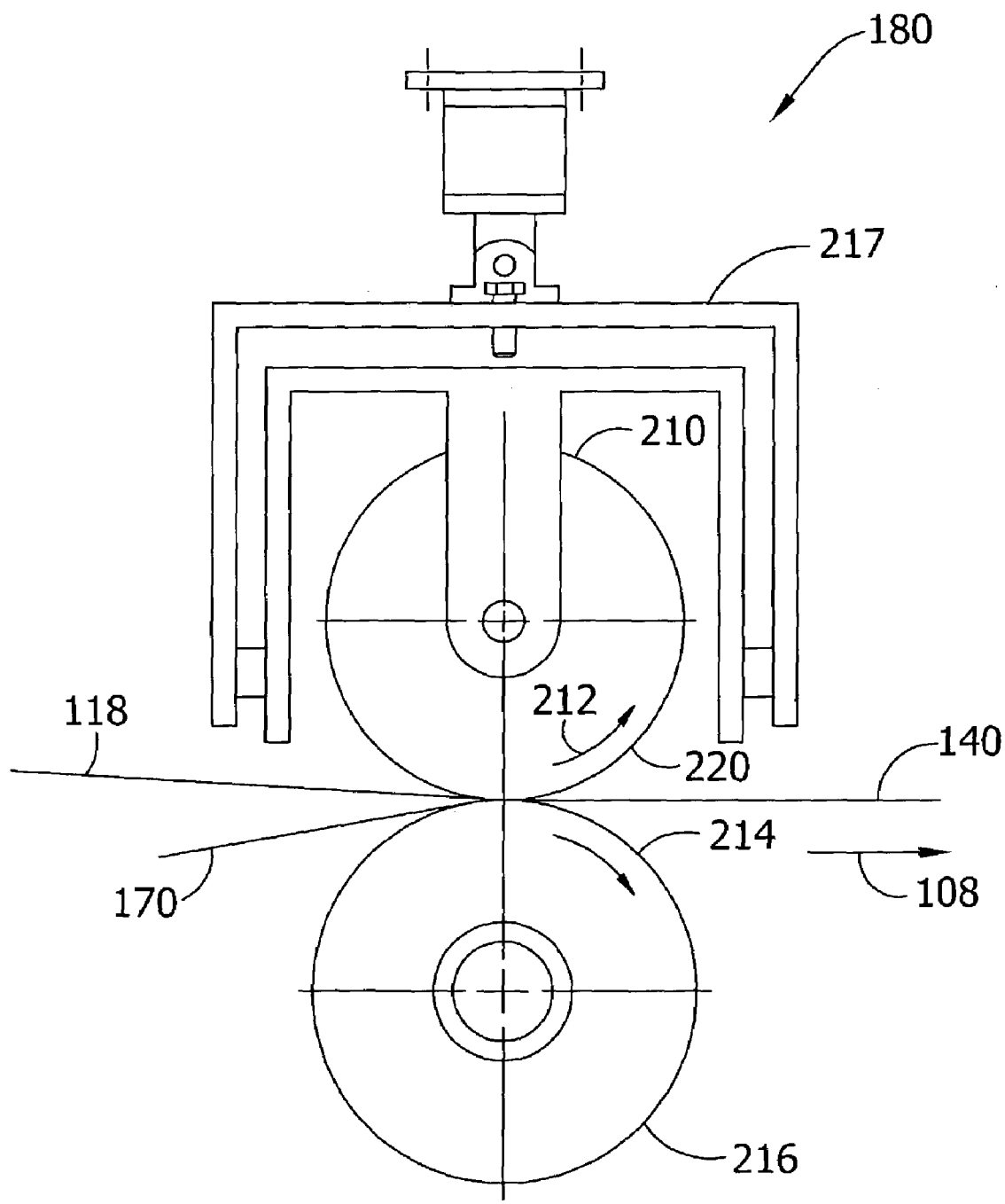
FIG. 6 is a schematic side elevation view of a fastening component bonding device of the apparatus of FIG. 4.

FIG. 6 illustrates one embodiment of the ultrasonic bonding device 180 in which the components (e.g., the fastener materials 160, 170 and strips 118 of side panel material 116) to be bonded together are passed through a nip defined by an anvil roll 210 and a opposed bonding roll 216. The anvil roll 210 is rotatably mounted and is connected to a support structure 217 by any suitable means, such as by conventional bearings, for rotation in the direction indicated by arrow 212. In general, the anvil roll 210 may be made from any metal having suitable mechanical properties. Desirably, the anvil roll 210 is made of hardened steel. In one embodiment, the bonding roll 216 comprises a rotary ultrasonic horn (not shown). In an alternative embodiment, the anvil roll 210 can include the rotary ultrasonic horn. Representative examples of rotary ultrasonic horns which can be used are described in commonly assigned U.S. Pat. No. 5,096,532 to Neuwirth et al. and U.S. Pat. No. 5,110,403 to Ehlert, which are herein incorporated by reference. In general, the rotary ultrasonic horn may be made from any metal having suitable acoustical and mechanical properties. Suitable metals include aluminum, monel, titanium and some alloy steels. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A.

The anvil roll 210 of the illustrated embodiment has a circumferential outer anvil surface 220 configured for bonding the fastener materials 160, 170 and the strips 118 together at discrete bond points arranged in a predetermined bond pattern. As representatively illustrated in FIGS. 7 and 8, the anvil surface 220 of the anvil roll 210 has a plurality of projections 222 extending outward therefrom. The projections 222 may extend completely across the width of the anvil surface 220 or, in the alternative, the projections may be disposed on only a portion of the anvil surface 220. In one embodiment, the projections are circular pins each having a diameter in the range of about 0.02 to about 0.1 inches (e.g., about 0.5 to about 2.54 mm), and more desirably in the range of about 0.03 to about 0.05 inches (e.g., about 0.76 to about 1.27 mm, and still more desirably about 0.04 inches (about 1.0 mm). However, the projections 222 can be sized in cross-section other than as set forth in the above range, and/or can have other shapes, such as square, S-shape, hexagon or other useful shapes.

The projections 222 of the anvil roll 210 press the fastener materials 160, 170 and the strips 118 against the bonding roll 216 to bond the materials together at discrete bond points. Alternatively, the anvil surface 220 may have a plurality of depressions disposed therein such that the remaining surface area of the anvil surface 220 presses the fastener materials 160, 170 against the bonding roll 216 to bond the materials together in a continuous bond pattern. The bond pattern may include projections 222 arranged in any repeating or arbitrary pattern depending upon the desired bonding configuration. Particular ultrasonic bond patterns comprising bonds which are compatible with the mechanical fastening of materials are disclosed in co-assigned U.S. Pat. No. 5,660,666 issued Aug. 26, 1997 to Dilnik et al., which is incorporated herein by reference. In an alternate embodiment, a bonding surface 214 of the bonding roll 216 may also have a plurality of projections thereon.

The projections 222 of the illustrated embodiment are disposed about the circumference of the anvil surface 220 so as to form discrete circumferential segments having different densities of projections. For example, in the illustrated embodiment the anvil surface 220 comprises a first segment 230 containing projections 222 positioned in a pattern defining a first density of projections. The anvil surface 220 further comprises a second segment 232 containing projections 222 positioned in a more dense pattern than the pattern in the first segment 230. In the first segment 230, the projections 222 desirably comprise less than or equal to about 20 percent of the surface area of the anvil surface 220 within the first segment, more desirably less than or equal to about 6 percent of the surface area of the anvil surface within the first segment, still more desirably between about 3.4 and about 4.5 percent of the surface area, and even more desirably about 3.9 percent of the surface area of the anvil surface within the first segment. In the second segment 232, the projections 222 desirably comprise between about 1 and about 30 percent of the surface area of the anvil surface 220 within the second segment, more desirably between about 3 and about 10 percent of the surface area, still more desirably between about 3.6 and about 5.4 percent of the surface area and even more desirably about 4.5 percent of the surface area of the anvil surface within the second segment.

Figure 7:
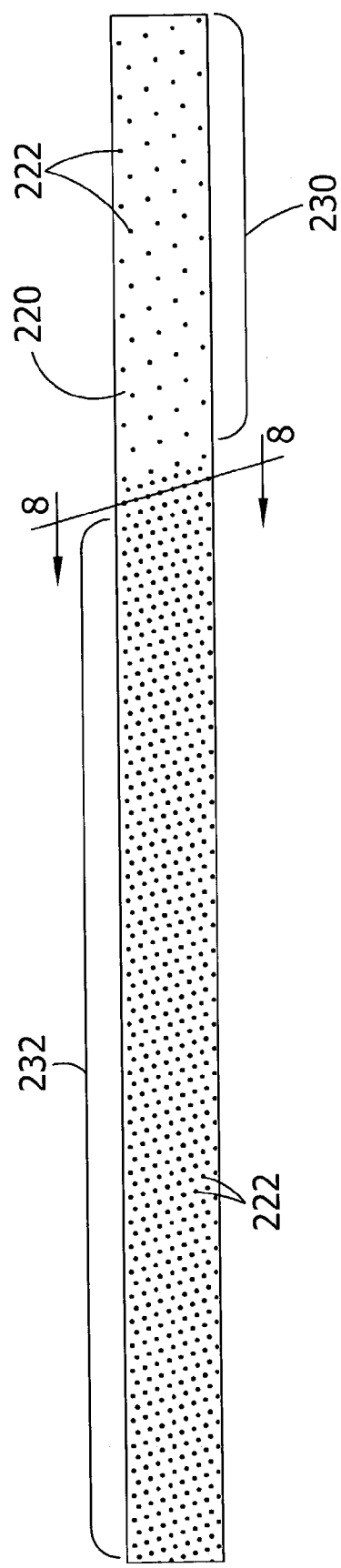
FIG. 7 is a flat view of a circumferential outer surface of an anvil roll of the bonding device of FIG. 6.
Figure 8:
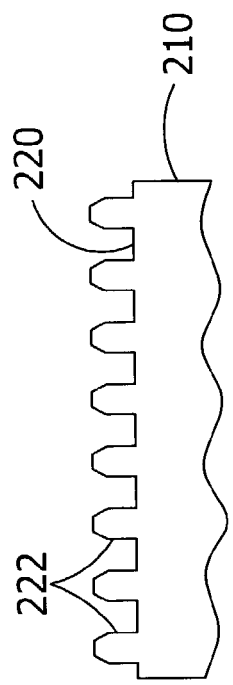
FIG. 8 is a fragmented cross-section taken in the plane of line 8—8 of FIG. 7.

As illustrated in FIG. 7, the projections 222 are arranged in a predetermined pattern within the first segment 230 and arranged in a similar, but more dense pattern within the second segment 232. It will be understood that other arrangements of projections 222 are contemplated. For instance, the projections in the second segment 232 can be arranged in a pattern having a lower density of projections than in the first segment 232. In another embodiment, different sizes (e.g., diameters) of projections 222 may be used in the different segments such that the patterns and densities are substantially the same but the area bonded by the projections 222 is greater in the second segment 232. The differing densities of the similarly sized projections 222 in the first and second segments 230, 232 shown in FIG. 7 is used to achieve a percent bonded area on the second fastening components 84 which is greater than the percent bonded area on the first fastening components 82 as described above.

Because the first and second fastening components 82 and 84 are disposed at the same selected cross machine direction locations, a single pair of bonding devices (e.g., two of the ultrasonic bonding devices 180 shown in FIG. 6) disposed on opposite sides of the machine center line and at the same selected cross-machine direction locations as the fastening components is all that is needed to bond the fastening components to the side panel strips 118. However, it is understood that where the fastening components 82, 84 are located at different cross-machine direction locations, the bonding apparatus may comprise two pair of bonding devices 180, e.g., with two bonding devices located on each side of the machine center line in cross-machine direction spaced relationship with each other corresponding to the cross-machine spacing between the fastening components. In such an embodiment, the first bonding segment 230 would comprise all or part of the anvil surface 220 of one device 180 on each side of the machine center line and the second bonding segment 232 would comprise all or part of the anvil surface of the other bonding device on each side of the machine center line.

In the illustrated embodiment, the size (e.g., diameter) and rotational speed of the bonding devices 180 can provide a timed, non-uniform bonding of the fastening components to the side panel material 116. For example, the bonding devices 180 can be registered with respect to the product assemblage 113 such that the anvil roll 210 provides a relatively higher degree of bonding which begins while disposed on one fastening component (such as 84 in FIG. 5), continues through the region where the product assemblage 113 will subsequently be cut (see cut line 159 in FIG. 5), and a lower degree of bonding on another fastening component (such as 82). Thus, the bonding devices 180 can be adapted to create relatively more bonds or stronger bonds between the fastening components 82, 84 and the side panel material 116 when the side panel material 116 reaches a particular location in the machine direction 108.

The bonding devices 180 can form a regular or irregular pattern of mechanical bonds that permanently bond the fastening components to the side panel strips 118. The width of the anvil roll 210 may be equal to the width of the first fastening components 82 and/or the second fastening components 84. Alternatively, the width of the anvil roll 210 may be greater than the width dimension of the first fastening components 82 and/or the second fastening components 84, in which case additional portions of the side panel strips 118 (and hence the side panels 34, 134) transversely inward and/or outward from the fastening components may have bond points 87 formed therein as shown in FIG. 9. Still alternatively, the width of the anvil roll 210 may be less than the width of the first fastening components 82 and/or the second fastening components 84, in which case the bonding-devices 180 may not bond the entire width dimension of the fastening components to the side panel strips 118 (and hence the side panels 34, 134) as shown in FIG. 10.

The strips 118 of side panel material 116 can be trimmed if desired, for example to provide angled and/or curved leg end edges 70 in the back waist region 24 (FIGS. 2 and 3). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled pairs of training pants 102 moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels.

The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

EXPERIMENT 1

A peel test was conducted to determine the peel strength of engaged fastening components of sample training pants having fastening components secured to the side panels of the training pants. That is, the peel test as referred to herein is a measurement of the force required to disengage hook and loop fasteners from one another.

In particular, for each sample pair of training pants, a ½ inch wide CS-600 hook fastener material commercially available from 3M Company, Minneapolis, Minn. U.S.A was initially adhered to each front side panel of the training pants. A 21 mm wide 2.0 osy (ounces per square yard) (67 gsm) point un-bonded (PUB) loop fastener material commercially available from Kimberly-Clark Worldwide, Inc., Neenah, Wis., U.S.A. was initially adhered to each of the back side panels of the training pants. The front and back side panels were constructed of an SBL.

The hook and loop fasteners were then either ultrasonically bonded to the respective side panels using one of various different percent bonded areas as set forth in the Table below, or passed through a nip assembly without ultrasonic bonding to simply press the hook and loop fasteners and side panels together. The ultrasonic bonding device was substantially similar to that described above and included an anvil roll with projections which were generally circular in cross section, having a diameter of about 0.040 inches, and arranged in diagonal rows about the outer surface of the anvil roll. The side panels to which the hook and loop fasteners were secured were then cut from the respective pants and paired in various combinations as set forth in the Table below. Each respective pair of hook and loop fasteners were engaged together to form a test sample and the peel test was then performed on each test sample to determine the peel strength between the engaged fasteners. More particularly, each test sample was placed in a suitable peel test apparatus, such as a Sintech 2 tester available from Sintech Corporation of Cary, N.C., U.S.A., an Instron Model TM available from Instron Corporation of Canton, Mass., U.S.A, or a Thwing-Albert Model INTELLECT II available from Thwing-Albert Instrument Co. of Philadelphia, Pa., U.S.A.

The test apparatus has a pair of clamps aligned along a common axis or plane, such as a vertical plane, with each clamp comprising a suitable pair of jaws for clamping the test sample. The fastening components of each test sample were disengaged (e.g., pulled apart) from each other at one end of the sample, with one fastening component then being clamped by the jaws of one clamp and the other fastening component being clamped by the jaws of the other clamp. The clamps are initially about 30 mm apart. The clamps are then moved apart from each other at a constant rate of about 500 mm/min, to pull the engaged fastening components apart at a separation angle of about 180 degrees.

The test is conducted over a test length starting with the engaged fastening components pulled apart approximately 0.40 inches and continuing until a total of about seven inches of the fastening components have been pulled apart. The peel strength of the sample is reported as the average load, in grams, over a specified smaller portion of the test length to reduce variability from handling the ends of the sample. For example, for the test samples cut from sample training pants prepared for the present test, the peel strength is the average load, in grams, starting from when approximately 2.40 inches of the engaged fastening components has been pulled apart and continuing until a total of about six inches of the fastening components has been pulled apart.

The results of the peel test are provided in the Table below. Twenty test samples (e.g., ten taken from the left hand side of a pair of pants and ten taken from the right hand side thereof) were tested for each of the different sample combinations identified in the Table, and the results were averaged.

TABLE 1

| Sample | Hook Percent Bonded Area | Loop Percent Bonded Area | Side | Engagement Peel Ave. (grams) |
|---|---|---|---|---|
| 1 | Rubber Nip | Rubber Nip | Left | 66.3 |
|   |            |            | Right | 81.9 |
| 2 | 4.5% | 4.5% | Left | 59.8 |
|   |      |      | Right | 56.2 |
| 3 | 4.5% | Rubber Nip | Left | 73.6 |
|   |      |            | Right | 84.8 |
| 4 | 4.5% | 2.25% | Left | 83.0 |
|   |      |       | Right | 86.9 |
| 5 | Rubber Nip | 4.5% | Left | 46.5 |
|   |            |      | Right | 41.1 |

As is evident from the peel test results, the peel strength between the hook and loop fasteners was greatest in Samples 3 and 4 where the percent bonded area of the hook fasteners was greater than the percent bonded area of the loop fasteners. However, simply pressing the loop fastener to the side panel without ultrasonic bonding, as in Sample 3, increases the risk that the loop fastener will undesirably separate from the side panel as a result of various forces applied during wear.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An article comprising:
a first waist region, a second waist region and a crotch region disposed between and interconnecting the first and second waist regions;
at least one first fastening component secured to the article generally at the first waist region within an attachment region of the first fastening component, said attachment region having an area, a bonded portion of the first fastening component within the attachment region being mechanically bonded to the article and the remaining portion of the first fastening component within the attachment region being substantially mechanically unbonded to the article, the bonded portion having an area within the attachment region, a ratio of the area of the bonded portion to the area of the attachment region defining a percent bonded area of the first fastening component within said attachment region; and
at least one second fastening component secured to the article and adapted for releasable engagement with the first fastening component to assemble said article, the second fastening component being secured to the article generally at the second waist region within an attachment region of said second fastening component, said attachment region having an area, a bonded portion of the second fastening component within the attachment region being mechanically bonded to the article and the remaining portion of said second fastening component within the attachment region being substantially mechanically unbonded to the article, a ratio of an area of the bonded portion to an area of the attachment region defining a percent bonded area of the second fastening component within said attachment region, the percent bonded area of the first fastening component being less than the percent bonded area of the second fastening component.

2. An article as set forth in claim 1 comprising a pair of said first fastening components secured to the article at the first waist region thereof in spaced relationship with each other, and a pair of said second fastening components secured to the article at the second waist region thereof in spaced relationship with each other and adapted for releasable engagement, each of said second fastening components being releasably engageable with a corresponding one of the first fastening components.

3. An article as set forth in claim 1 wherein the article has laterally opposite first side panels at said first waist region and laterally opposite second side panels at the second waist region, the first fastening components being secured respectively to the first side panels and the second fastening components being secured respectively to the second side panels.

4. An article as set forth in claim 1 wherein the percent bonded area of the first fastening component within the attachment region thereof is less than or equal to about six percent.

5. An article as set forth in claim 1 wherein the percent bonded area of the second fastening component within the attachment region thereof is in the range of about three to about ten percent.

6. An article as set forth in claim 4 wherein the percent bonded area of the first fastening component within the attachment region thereof is in the range of about 3.4 to about 4.5 percent.

7. An article as set forth in claim 1 wherein the percent bonded area of the second fastening component within the attachment region thereof is in the range of about one to about thirty percent.

8. An article as set forth in claim 5 wherein the percent bonded area of the second fastening component within the attachment region thereof is in the range of about 3.6 to about 5.4 percent.

9. An article as set forth in claim 1 wherein the bonded portion of the first fastening component within the attachment region thereof comprises a plurality of discrete bond points at which the first fastening component is mechanically bonded to the article, the bond points being arranged in a generally uniform density within at least a portion of the attachment region of said first fastening component.

10. An article as set forth in claim 9 wherein the bond points within the attachment region of the first fastening components together define an average bond point density of the first fastening component within the attachment region thereof, said average bond point density being in the range of about 1 $cm^2$ to about 50 $cm^2$.

11. An article as set forth in claim 1 wherein the percent bonded area of the first fastening component within the attachment region thereof is less than or equal to about twenty percent.

12. An article as set forth in claim 11 wherein the percent bonded area of the second fastening component within the attachment region thereof is in the range of about one to about thirty percent.

13. An article as set forth in claim 1 wherein the bonded portion of the second fastening component within the attachment region thereof comprises a plurality of discrete bond points at which the second fastening component is mechanically bonded to the article, the bond points being arranged in a generally uniform density within at least a portion of the attachment region of said second fastening component.

14. An article as set forth in claim 13 wherein the bond points within the attachment region of the second fastening components together define an average bond point density of the second fastening component within the attachment region thereof, said average bond point density being in the range of about 1 $cm^2$ to about 50 $cm^2$.

15. An article as set forth in claim 1 wherein the bonded portion of the first fastening component within the attachment region thereof comprises a plurality of discrete bond points at which the first fastening component is mechanically bonded to the article and which together define an average bond point density of the first fastening component within said attachment region, the bonded portion of the second fastening component within the attachment region thereof comprising a plurality of discrete bond points at which the second fastening component is mechanically bonded to the article and which together define an average bond point density of the second fastening component within said attachment region thereof, the average bond point density of the first fastening component being less than the average bond point density of the second fastening component.

16. An article as set forth in claim 15 wherein the bond points at which the first fastening component is bonded to the article each have a cross-sectional area which is substantially the same as a cross-sectional area of each of the bond points at which the second fastening component is bonded to the article.

17. An article as set forth in claim 1 wherein the bonded portion of the first fastening component within the attachment region thereof comprises a plurality of discrete bond points at which the first fastening component is mechanically bonded to the article, the bonded portion of the second fastening component within the attachment region thereof comprising a plurality of discrete bond points at which the second fastening component is mechanically bonded to the article, the bond points at which the first fastening component is bonded to the article having a generally uniform cross-sectional area, the bond points at which the second fastening component is bonded to the article having a generally uniform cross-sectional area which is different from the cross-sectional area of the bond points at which the first fastening component is bonded to the article.

18. An article as set forth in claim 1 wherein the first fastening component is a loop fastener and the second fastening component is a hook fastener.

19. An article as set forth in claim 1 wherein at least one of the first and second fastening components is ultrasonically bonded to the article.

20. An article as set forth in claim 1 wherein the article is a pair of training pants.

21. An article as set forth in claim 1 wherein the first fastening component has a surface area, the area of the attachment region of the first fastening component being less than the surface area of the first fastening component.

22. An article as set forth in claim 1 wherein the second fastening component has a surface area, the area of the attachment region of the second fastening component being less than the surface area of the second fastening component.

23. An article as set forth in claim 1 wherein the first fastening component is a hook fastener and the second fastening component is a loop fastener.

* * * * *